United States Patent
Hickle

(10) Patent No.: US 7,034,692 B2
(45) Date of Patent: Apr. 25, 2006

(54) SYSTEM AND METHOD FOR TRANSPARENT EARLY DETECTION, WARNING, AND INTERVENTION DURING A MEDICAL PROCEDURE

(75) Inventor: Randall S. Hickle, Lubbock, TX (US)

(73) Assignee: Scott Laboratories, Inc., Lubbock, TX (US)

( * ) Notice: Subject to any disclaimer, the term of this patent is extended or adjusted under 35 U.S.C. 154(b) by 74 days.

(21) Appl. No.: 10/436,497

(22) Filed: May 13, 2003

(65) Prior Publication Data

US 2003/0214409 A1 Nov. 20, 2003

Related U.S. Application Data

(60) Provisional application No. 60/379,388, filed on May 13, 2002.

(51) Int. Cl.
*G08B 23/00* (2006.01)

(52) U.S. Cl. .............. 340/573.1; 600/301; 128/200.24

(58) Field of Classification Search ............ 340/573.1; 600/301, 323, 364, 529; 128/200.24
See application file for complete search history.

(56) References Cited

U.S. PATENT DOCUMENTS

| | | | | |
|---|---|---|---|---|
| 4,759,369 A | 7/1988 | Taylor | ......................... | 128/633 |
| 4,869,254 A | 9/1989 | Stone et al. | ................. | 128/633 |
| 5,046,491 A | 9/1991 | Derrick | .................. | 128/200.24 |
| 5,063,275 A | 11/1991 | Rosenfeld et al. | .......... | 250/343 |
| 5,156,159 A | 10/1992 | Lampotang et al. | ........ | 128/719 |
| 5,178,155 A | 1/1993 | Mault | .......................... | 128/718 |
| 5,179,958 A | 1/1993 | Mault | .......................... | 128/718 |
| 5,190,038 A | 3/1993 | Polson et al. | ................ | 128/633 |
| 5,632,281 A | 5/1997 | Rayburn | ...................... | 128/719 |
| 5,738,106 A | 4/1998 | Yamamori et al. | ........... | 128/719 |
| 5,836,300 A | 11/1998 | Mault | ...................... | 128/204.23 |
| 6,059,732 A | 5/2000 | Orr et al. | ...................... | 600/532 |
| 6,102,868 A | 8/2000 | Banner et al. | ............... | 600/484 |
| 6,135,107 A | 10/2000 | Mault | ...................... | 128/204.23 |
| 6,217,524 B1 | 4/2001 | Orr et al. | ...................... | 600/504 |
| 6,241,681 B1 | 6/2001 | Haryadi et al. | .............. | 600/504 |
| 6,251,082 B1 | 6/2001 | Rayburn | ...................... | 600/532 |
| 6,258,038 B1 | 7/2001 | Haryadi et al. | .............. | 600/504 |
| 6,272,905 B1 | 8/2001 | Drzewiecki | ................. | 73/53.01 |
| 6,305,212 B1 | 10/2001 | Drzewiecki | ................. | 73/23.07 |
| 6,751,499 B1* | 6/2004 | Lange et al. | ................. | 600/544 |
| 2001/0029340 A1 | 10/2001 | Mault et al. | ................. | 600/532 |
| 2002/0017996 A1* | 2/2002 | Niemiec | ................... | 340/573.1 |
| 2003/0233086 A1* | 12/2003 | Burns et al. | ................. | 604/512 |

FOREIGN PATENT DOCUMENTS

| | | |
|---|---|---|
| EP | 0 639 951 B1 | 3/1995 |
| WO | 99/45988 | 9/1999 |
| WO | 99/62403 | 12/1999 |
| WO | 01/56454 A2 | 8/2001 |

* cited by examiner

*Primary Examiner*—Jeffery Hofsass
*Assistant Examiner*—George A. Bugg
(74) *Attorney, Agent, or Firm*—Hogan & Hartson LLP

(57) ABSTRACT

The present invention relates, in general, to prevention of false, annoying, or oversensitive alarms, providing early detection by a sensitive test, generating silent, semi-overt, or overt alarm conditions and/or initiating early passive or active interventions to untoward events. The invention buys time by providing an early intervention in the event that a highly sensitive early detection is later confirmed by a specific test. A particular embodiment of the invention is directed to the early detection of hypoventilation, including apnea and airway obstruction, and the pausing or interrupting of an action such as drug delivery during medical procedures.

41 Claims, 9 Drawing Sheets

SYSTEM AND METHOD FOR TRANSPARENT EARLY DETECTION, WARNING, AND INTERVENTION DURING A MEDICAL PROCEDURE

CROSS-REFERENCE TO RELATED APPLICATIONS

This application claims priority under 35 U.S.C. §119(e) to U.S. Provisional Patent Application No. 60/379,388, "System and Method for Transparent Early Detection, Warning, and Intervention During a Medical Procedure," filed May 13, 2002, which is hereby incorporated by reference.

STATEMENT REGARDING FEDERALLY SPONSORED RESEARCH OR DEVELOPMENT

Not Applicable

REFERENCE TO A "MICROFICHE APPENDIX"

Not Applicable

BACKGROUND OF THE INVENTION

1. Field of the Invention

The present invention relates to prevention of false, annoying, or oversensitive alarms during medical procedures, providing early detection by a sensitive test, generating silent, semi-overt, or overt alarm conditions and/or initiating early passive or active interventions to untoward events.

2. Description of Related Art

In certain clinical incidents or emergencies, timely intervention may be critical to outcome. Earlier detection of a developing untoward clinical event facilitates timelier diagnosis and intervention and enhances the probability of a safe and minimally disruptive recovery. Sensitive tests and alarms, in general, assist in earlier detection. However, sensitive tests and alarms are also more prone to annoying, distracting and potentially disruptive false positive alarms. Thus, a medical device designer (or clinician in the case of user-adjustable alarms) generally compromises in setting alarm thresholds so that false positive alarms are minimized and true alarm conditions are detected. Much valuable time may be lost due to this compromise.

Correct assessment of gas exchange during procedures involving sedation and analgesia is important because respiratory depressants are often administered to patients undergoing painful medical procedures. Respiratory depressants, such as sedation and analgesia agents, can relax the soft tissue of the throat causing partial or complete airway obstruction in some patients, or blunt the respiratory drive, i.e., the urge to breathe when the blood level of carbon dioxide rises. If not diagnosed promptly, such conditions can quickly develop into a life-threatening situation. If a patient does not move a sufficient volume of gas containing oxygen into and out of the lungs then the patient will develop a deficiency in the oxygen supply to body tissue (hypoxia) which, if severe and progressive, is a lethal condition.

In many health care settings, clinicians assess respiratory gas exchange by using an elevated arterial partial pressure of carbon dioxide ($P_aCO_2$) as an indicator of incipient respiratory failure or prolonged airway obstruction. In this regard, the determination of $P_aCO_2$ is useful in optimizing the settings on ventilators, detecting life-threatening blood gas changes, and detecting the presence of airway obstruction in an anesthetized or sedated patient undergoing a medical procedure. The traditional method of obtaining arterial blood gas values is to extract a sample of arterial blood and measure $P_aCO_2$ using a blood gas analyzer. Arterial puncture with a needle to extract the arterial blood sample has inherent limitations: 1) arterial puncture carries a degree of patient discomfort and risk, 2) handling of the blood is a potential health hazard to health care providers, 3) significant delays are often encountered before results are obtained and, 4) measurements can only be made intermittently. Furthermore, blood $CO_2$ measurements do not immediately reflect changes in patient ventilation, so they may not detect airway obstruction in its early stages when it may still be corrected prior to the onset of adverse physiological consequences. Therefore, clinically, early or timely detection of hypoventilation via blood gas analysis is not practical and this approach might even be considered unsafe and ineffective.

Hypoventilation results from low or no minute ventilation (MV). Minute ventilation is the product of respiratory rate (RR) and tidal volume ($V_T$). Low MV may be caused by bradypnea (low RR) or apnea (no breathing; RR=0) or inadequate tidal volumes (resulting from, among others, airway obstruction, shallow breathing, insufficient $V_T$, $V_T$ less than dead space) or a combination of low $V_T$ and low RR. A fast RR does not exclude hypoventilation if $V_T$ is too small for effective ventilation of the lungs or less than the deadspace. Similarly, a large $V_T$ does not exclude hypoventilation if RR is too low for adequate minute ventilation.

Continuous invasive monitoring requires in-dwelling arterial lines that entail inherent problems such as, for example, sepsis or thrombosis. The nature and expense of this monitoring system excludes its application under routine care, restricting its use to intensive care units within a hospital facility. In-dwelling arterial lines providing real-time $P_aCO_2$ analysis are not able to tell the immediate status of a patient's ventilation, because there is a time delay between the onset of ventilatory insufficiency or hypoventilation and a subsequent rise in arterial carbon dioxide levels.

In current clinical practice, $P_aCO_2$ levels are indirectly inferred via capnometry, the measurement of $CO_2$ levels in the gas mixture breathed by a patient. If the $CO_2$ levels, in addition to being measured, are also graphically displayed as a $CO_2$ level vs. time plot, the technique is called capnography and the resulting plot is called a capnogram. A typical capnogram comprises three distinct phases during exhalation. Phase I reflects the clearing of $CO_2$-free gas from conducting airways which do not normally participate in gas exchange (i.e., airway dead space). Phase II is generated by exhalation of $CO_2$-free gas from conducting airways mixed with alveolar gas containing $CO_2$ because the alveolar gas has undergone gas exchange with arterial blood containing $CO_2$ at the alveolar membrane. Phase III reflects the exhalation of alveolar gas which has had time, through the process of diffusion, to equilibrate its partial pressure of $CO_2$ with the partial pressure of $CO_2$ in arterial blood.

Because the lung's airways are a dead-ended conduit, gas flow in the lungs follows a first in, last out principle. Thus the last amount of alveolar gas exiting the lungs during exhalation was the first in and has had the most time to equilibrate its partial pressure with the partial pressure of the equivalent substance in arterial blood, such as, among others, $CO_2$, $O_2$, volatile anesthetic, intravenous anesthetic, alcohol, medication and inert gas anesthetic. Thus, in healthy patients, alveolar gas exhaled during phase III is representative of the partial pressures of different substances dissolved in arterial blood. Further, the $CO_2$ component of alveolar gas exhaled during Phase III is generally a good indicator of the ventilatory status of a healthy patient.

When using capnometry or capnography, clinicians generally utilize the peak or end-tidal $CO_2$ ($P_{et}CO_2$) value as an estimate Of $P_aCO_2$. $P_{et}CO_2$ is indicative of the mean alveolar partial pressure of carbon dioxide from all functional gas exchange units of the lung, which, in turn, approximates $P_aCO_2$ in normal lungs. Because $CO_2$ readily diffuses from arterial blood into alveolar gas across the alveolar membrane, $P_{et}CO_2$ closely approximates $P_aCO_2$ when the lung has normal ventilation and perfusion. In addition to the information provided by the $P_{et}CO_2$, the shape of the capnogram also provides valuable diagnostic information regarding the respiratory ventilation.

Other techniques have been utilized for assessing patient blood gas levels with mixed results. Transcutaneous $CO_2$ sensors measure the partial pressure of $CO_2$ in tissue. The sensors are placed onto the skin of the patient and measure $CO_2$ diffusing through heated skin but have practical and theoretical limitations. Pulse oximetry is a widely used, non-invasive method for estimating the arterial oxygen carried in hemoglobin. Neither transcutaneous measurements of $CO_2$ nor pulse oximetry directly measures and reports the status of respiratory ventilation. Thus, transcutaneous $CO_2$ measurement and pulse oximetry may be late to diagnose an impending problem. In the case of pulse oximetry, once the condition of low oxygen is detected, the problem already exists, and once the transcutaneous $CO_2$ measurement is elevated, it indicates that hypoventilation has already existed for a period of time sufficient for a rise in the partial pressure of tissue $CO_2$.

Capnometers have been used with some success as a means for detecting and avoiding the severe complications associated with hypoventilation, partial or complete airway obstruction, bradypnea and apnea. Systems assessing proper gas exchange based on predetermined or user-adjusted carbon dioxide thresholds detect instances of hypoventilation or airway obstruction. In general, the $CO_2$ level must exceed a lower threshold (indicating sufficient gas exchange and ruling out apnea) and stay below a higher threshold (indicating adequate ventilation and ruling out high end-tidal $CO_2$ concentrations due to, for example, hypoventilation). However, capnometers are often prone to false positive alarms.

A false positive alarm occurs when a system indicates that a potentially dangerous situation has arisen, when in fact, it has not. False positive alarms may occur in situations where a change in $CO_2$ levels is unrelated to respiratory gas exchange. Such misleading alarms may result from a patient talking, breathing through an unmonitored orifice, or dilution of the exhaled gases at the sampling source. False positive alarms may occur in systems where a predetermined carbon dioxide threshold may be set at an arbitrary point that may not be representative of inadequate gas exchange. Systems prone to false positive alarms are often deactivated by clinicians or simply ignored, putting a patient at risk if a truly life threatening situation occurs.

During inhalation, a patient breathing ambient air will inhale room air containing a negligible amount of carbon dioxide (0.03% v/v) that will not register on clinical capnometers. The beginning of an exhalation may be nearly indistinguishable from the inhalation phase due to a patient breathing out dead space gas that has not mixed with alveolar $CO_2$ found deeper in the lungs. As a patient continues to exhale, alveolar $CO_2$ will be expelled from the lungs and the $CO_2$ level will cross a lower threshold as he/she continues to exhale, eventually reaching a plateau or peak referred to as "end-tidal" $CO_2$. As a patient begins to inhale, carbon dioxide levels will drop below the lower threshold level due to a negligible amount of $CO_2$ in room air. The period between a crossing of a threshold on an exhalation upstroke and a crossing of the same threshold on a subsequent exhalation upstroke is usually considered as a full breath or respiratory cycle.

When hypoventilation is due to adequate $V_T$ but low RR, the $CO_2$ level will cross a lower $CO_2$ threshold and eventually the $P_{et}CO_2$ will exceed a higher $CO_2$ threshold as alveolar $CO_2$ concentration rises because $CO_2$ is accumulating in the alveoli as a result of inadequate minute ventilation. When hypoventilation is due to adequate RR or fast RR but low $V_T$ (shallow breathing or panting), the $CO_2$ level may never cross the lower $CO_2$ threshold because the exhaled gas is comprised mainly of dead space gas devoid of $CO_2$ and is at most mixed with a minimal amount of alveolar $CO_2$.

Many $CO_2$ monitoring systems are programmed to initiate an alarm in the event that a patient does not complete a sufficient number of respiratory cycles (breaths) within a predetermined time window. False negative alarm conditions may result from such systems, where inadequate gas exchange is occurring in a patient but a system fails to recognize a potentially life threatening event. The fact that the exhaled $CO_2$ level crosses a lower $CO_2$ threshold within a predetermined time window is not sufficient to assure that a patient is experiencing adequate gas exchange. For example, a patient with a significant partial airway obstruction may break through a blockage in order to take a short (physiologically insignificant) breath, registering with a capnometer system that a patient is breathing at a normal rate within a predetermined time window such that an airway obstruction may remain undetected. Breaths taken by a patient, though of normal frequency, may not be of adequate volume to provide sufficient oxygen supply and carbon dioxide elimination to maintain a healthy state.

An untoward event will usually generate an alarm to alert a clinician. Generally, a clinician will respond to an alarm by taking an appropriate corrective action. Thus, an untoward event generates two distinct actions: an alarm (usually automated) and a response (usually manual but it may also be automated). The terms "response" and "alarm" will be used consistently herein according to the definitions above. The response of a clinician usually also involves turning off the alarm because of its annoying nature, requiring a superfluous action that does not directly contribute to patient care. In the event of a false positive alarm, even more time and motion are wasted in activities that do not directly contribute to, and may detract from, patient care. False alarms may also devalue the benefit and credibility of alarms (the "cry wolf" syndrome).

With some systems featuring automated responses (such as interruption of drug delivery) to alarms, an audible or visual alarm generally accompanies an automated response. A design rationale for having an overt alarm (a potential annoyance) generally accompany an automated response (a potential benefit to a busy, multi-tasked clinician) is that an untoward condition should not be masked from a clinician, even if the system has initiated an automated corrective response. Therefore, a tightly set automated response that is designed to intervene early and/or frequently to provide better control of a given parameter will, in general, also generate more frequent and potentially disruptive alarms.

In the past, increasing the sensitivity of monitoring systems created a greater probability of detecting untoward events but also increased the probability of false alarms triggered by patient conditions that do not warrant the attention of a busy, multi-tasked clinician. Decreasing the sensitivity of monitoring systems diminishes the incidence of false alarms but increases the probability that critical untoward events may be missed.

False positive alarms may be caused by an over-sensitive alarm algorithm that is vulnerable to spurious data or a data artifact. Over-sensitivity may be due to a short averaging period, or no averaging, of carbon dioxide. False negative alarms are generally attributable to low specificity, where specificity relates to determining the actual significance of information received via patient monitoring. High specificity may reduce alarms associated with spurious data or over-sensitivity, yet may also hide those patient episodes that constitute truly life-threatening situations.

A further example of potential false negative alarm episodes occurs when a patient experiences ineffective hyperventilation, characterized by high respiratory rates with very low tidal volumes. Breathing at very low tidal volumes expels mainly dead space gas from the upper airway that has not, or minimally, mixed with alveolar $CO_2$. The next inhalation of a small tidal volume is sequestered in the dead space formed by the upper airway and never or barely reaches the alveoli where gas exchange occurs. During hyperventilation, a carbon dioxide threshold may be just reached, indicating a breath to the $CO_2$ monitor. However, a patient may not be inhaling sufficient oxygen or eliminating sufficient carbon dioxide for adequate gas exchange.

Because even short acting drugs exhibit a finite half-life, it is desirable to reduce or shut off drug delivery as early as possible in the event of an untoward patient state, providing in effect an "early response" system so that an untoward condition can be promptly reversed. In the context of systems integrating ventilatory monitoring and sedative and/or analgesic drug delivery, deactivation of drug delivery early in the development of a life-threatening condition is desirable.

It would therefore be advantageous to provide a respiratory gas exchange monitoring system for detecting partial or complete airway obstruction or depressed respiratory drive to breathe comprising high sensitivity and high specificity, thus diminishing the incidence of false positive and false negative alarms. It would be even further advantageous to provide a respiratory gas exchange monitoring system integrated with a sedative and/or analgesic drug delivery system that deactivates drug delivery at the onset of a potentially dangerous patient episode.

It would be further advantageous to provide a respiratory gas exchange monitoring system that accurately measures and indicates carbon dioxide elimination during every breath. It would be further advantageous to provide a respiratory gas exchange monitoring system that is capable of estimating overall carbon dioxide elimination during a procedure in such a way as to determine whether exhaled carbon dioxide levels are relatively constant. It would be further advantageous to provide a respiratory gas exchange monitoring system integrated with a drug delivery system designed for operation by non-anesthetists that provides additional patient safety features.

BRIEF SUMMARY OF THE INVENTION

The present invention provides an anthropomorphic automated alarm and response paradigm that allows clinicians to enjoy the benefits of automated responses to adverse events concerning their patients that is not prone to false alarms and improper responses. More particularly, the present invention comprises a system for use during the performance of a medical procedure on a patient that monitors the ventilatory conditions of a patient and provides automated responses to certain of those conditions in a manner that is both highly sensitive in detecting adverse events and that reduces false positive and false negative alarms in a manner that is transparent, or nearly so, to the user. In particular embodiments of the present invention, the conditions that the system monitors are related to the gas exchange of the patient where certain suspect values of the gas exchange trigger the system's automated responses. Once triggered by the existence of those suspect ventilatory conditions should they occur, the system of the present invention initiates an automated response and then enters into a hypervigilant state during which it continues to acquire and evaluate data regarding the patient's conditions. During the hypervigilant state, the system may perform additional tests of high specificity to confirm whether an adverse condition truly exists with the patient. Such adverse conditions suspected by the system may include partial or complete airway obstruction, bradypnea, apnea, and hypoventilation. These additional tests may be related to the same data, such as gas exchange or capnometry data, that is collected by the system throughout the procedure or they may be related to different data the acquisition of which begins when the system enters the hypervigilant state.

The automated responses initiated by the system of the present invention may be passive or active interventions in the continuance of the medical procedure or part of that procedure. Should an adverse condition truly exist, the system may continue the intervention and may initiate further interventions or it may even halt the entire medical procedure or parts of that procedure. For example, in particular embodiments of the present invention, the system operates in conjunction with a drug delivery system for providing sedation or analgesia to the patient during a medical procedure and acts to pause the delivery of drugs to the patient upon the detection of the suspect conditions. In these embodiments, the system may shut down the drug delivery altogether upon the determination during the hypervigilant state that a true alarm condition exists with the patient. In this manner the invention deactivates drug delivery in situations in which the continuance of drug delivery may be life-threatening to the patient, because the drug delivery itself may be causing the true alarm conditions to exist with the patient. A further example of a passive intervention in a medical procedure is where the system of the present invention pauses the delivery of shock waves to kidney stones during extra-corporeal shock wave lithotripsy when adverse effects on cardiac function are suspected. Examples of active interventions that may be employed by the system of the present invention include initiating sodium nitroprusside infusion and continuous positive airway pressure (CPAP) administration.

The system may determine during the hypervigilant state that an adverse condition does not truly exist, i.e. the initial suspect conditions were merely a false alarm. In such situations, the system of the present invention may then end the interventions in the continuance of the medical procedure and may return the procedure to its state just prior to the interventions or to where it would have been had no interventions taken place. The invention thus provides early triggering of corrective interventions based on patient conditions that may be indicative of truly adverse events without waiting the few seconds it may take the system or the user to determine that a truly adverse event indeed exists. In this manner, the invention supplies added safety to a medical procedure while ensuring a highly sensitive analysis of patient data is completed before a permanent intervention in the procedure is automated. This invention is applicable where the costs of unnecessary interventions that it performs in a medical procedure (those during false alarms) are low, i.e., where no harm is done to the patient or the procedure by the temporary intervention.

The initial interventions before the hypervigilant state is entered by the system may be accompanied by silent or semi-overt alarms or may be otherwise transparent to the user. Upon a true positive alarm, the user may be notified by the system of the adverse conditions of the patient and of the continued and/or further automated responses. If the system determines during the hypervigilant state that the suspect conditions that triggered the initial alarm response were not indicative of a truly adverse event, then no overt or annoying alarms are put in front to the user. In this manner, only true positive alarms and not false or disruptive alarms are portrayed to the user.

The anthropomorphic alarm and response paradigm of the present invention is analogous to a anesthesia provider's reaction during a surgical procedure whereby he may lean forward to look closely at a given parameter that seems to be out of the norm (i.e., be hypervigilant) and then may reduce the dose of volatile anesthetic given to the patient (i.e., initiate an early intervention) all the while not raising an alarm to the surgeon until he has better assessed the parameter to see if it truly represents a serious condition.

DETAILED DESCRIPTION OF THE INVENTION

Figure 1:
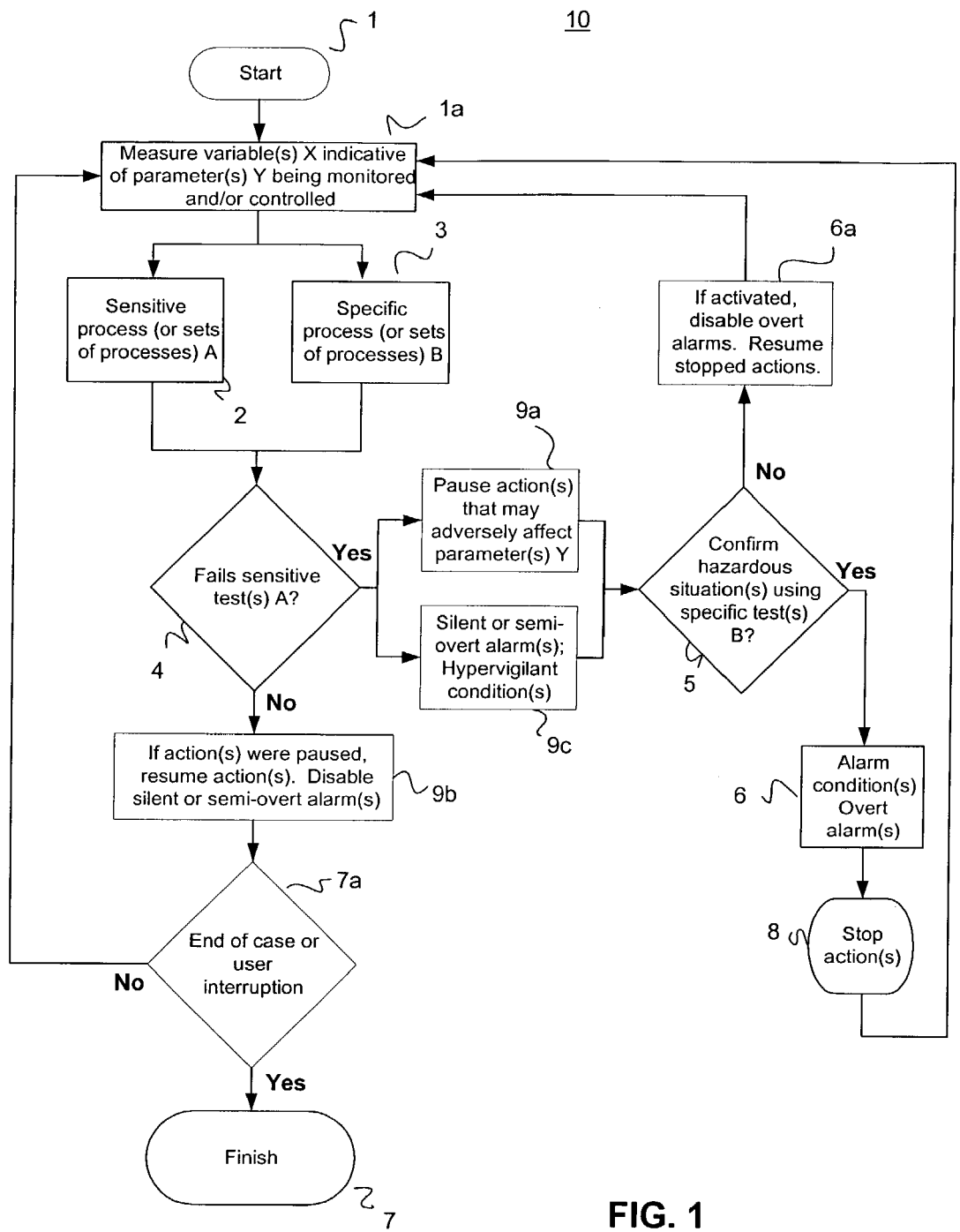
FIG. 1 depicts a general embodiment of a method performed by the system of the present invention.

FIG. 1 represents a general embodiment of a method performed by the system of the present invention. After a start 1, method 10 comprises measurement 1a of a variable or parameter X that is indicative of a parameter or property Y that a clinician desires to monitor and/or control. In certain situations (with blood pressure for example), it may be possible to measure Y directly so that X is the same as Y. In other cases, it may not be clinically practical to measure a parameter Y directly and therefore a variable or parameter X is measured that is an indirect estimate of a status and/or trend of parameter Y. For example, $CO_2$ and $S_pO_2$ measurements may be taken to serve as indicators of ventilation and oxygenation respectively. For the sake of simplicity, FIG. 1 only shows one variable X being measured, however the concept of the present invention fully contemplates measurement of multiple variables X that are direct or indirect measurements of a plurality of parameters Y being simultaneously monitored and/or controlled. The frequency at which measurement 1a is performed can be 50–100 Hz, but could also be slower or faster depending on the characteristics of the parameter X being measured.

Processes or sets of processes 2 and 3 are subsequently performed on a measured value of X. Sensitive process or sets of processes A 2 use the measured value of X to generate derived values of X that are sensitive indicators of the status and/or trend of Y that are also relatively immune from artifactual or spurious data. An example of sensitive process 2 may be averaging the value of X over moving time windows of the most recent 6, 12, 20, 30 and n seconds. Specific process or sets of processes B 3 use the measured value of X to generate derived values of X that are specific indicators of the status and/or trend of Y that are also relatively immune from artifactual or spurious data. An example of specific process 3 may be the cumulative addition of the value of X over a plurality of time periods starting at different start times. The invention also contemplates placing specific process or sets of processes 3 between sensitive test(s) 4 and specific test(s) 5 such that specific process or sets of processes 3 are only executed upon failure of sensitive test(s) 4.

Derived values of X generated by sensitive process or sets of processes 2 are used to perform sensitive test(s) 4. For purposes of example, step 4 may comprise comparing derived values of X obtained from step 2 to a predetermined threshold. If test(s) 4 are passed, method 10 checks if any actions were paused and resumes them, if they were paused. Method 10 leaves the actions unaltered if no actions were previously paused; any silent or semi-overt alarms are deactivated. Method 10 then proceeds to check if an end of case or user interruption 7a is present. If an end of case or user interruption 7a is present, method 10 transitions to finish 7 and is concluded. If an end of case or user interruption 7a is not present, method 10 loops back to measurement of X 1a, completing a normal, uneventful (i.e., no failed sensitive test) path.

If one or more of sensitive tests 4 fails, method 10 transitions into a hypervigilant condition 9c that may include silent and/or semi-overt alarms. A semi-overt alarm is a low-key alarm that does not attempt to grab the attention of a user because an alarm condition has not yet been confirmed and still has a probability of being a false alarm. An experienced user may direct his or her attention to a location of a semi-overt alarm to obtain data regarding the status and operation of a system. An example of a semi-overt alarm may be a non-flashing visual indicator such as an LED of a white or neutral color. An example of a silent alarm is an alarm response accompanied by no visual or audible indication or other attention-getting feature of failure of tests 4.

A pause 9a of any actions that may adversely affect parameter(s) Y is initiated upon failure of sensitive test(s) 4. An early intervention in the form of a pause or initiation of an action is especially beneficial in the case of conditions that exhibit an inertial component and take discrete and clinically significant amounts of time to identify and/or reverse. Examples of actions that may be paused are infusion of respiratory depressant drugs (such as propofol) if Y is ventilation; infusion of sedatives if Y is monitored patient responsiveness; infusion of blood pressure altering drugs if Y is blood pressure or intracranial pressure; initiation of CPAP in response to diagnosed airway obstruction; initiation of supplemental O2 delivery in response to ventilatory insufficiency and/or oxygen desaturation and a titrator for control of blood pressure that silently pauses or initiates sodium nitroprusside infusion in the event of a spike of BP downward or upward respectively. The invention is also applicable to similar systems for treatment of hypotension using levophed, neosynephrine, dopamine, or other inotropic/vasoconstrictive compounds where the infusion rate is increased in the event of a spike downward of blood pressure or decreased if the blood pressure spiked upward and then reassessed with further data. In the event of an early detection of a possible arrhythmia, the invention could be applied to charge the capacitor plates (a time-consuming process) of an internal or external defibrillator and then either give defibrillation/cardioversion joules if the event turns out (with more data) to be a true positive or drain the capacitor charge if the event turned out to be false positive.

Confirmation test 5 uses derived values of X obtained from specific process or sets of processes 3 to confirm whether adverse conditions really exist. Confirmation test 5 could comprise, for example, comparing cumulative sums of X over set periods of time starting from a time of failure of sensitive test 4 to preset thresholds. If adverse conditions are not confirmed by confirmation test 5, method 10 loops back to measurement of X 1a, disabling 6a any active overt alarms along the way. As long as failure of sensitive test(s) 4 occurs, a pause of actions 9a is active; X is continuously measured and derived sensitive and specific values of X are updated to determine the status and/or trend of parameter(s) Y. If after actions have been paused, failure of sensitive test(s) 4 goes away, paused actions are resumed 9b.

If adverse conditions are confirmed by confirmation test 5, overt alarms are generated 6 and actions are stopped 8. Method 10 loops back to measurement of X to update the status and trend of X and the derived sensitive and specific values of X as indicators of the status and/or trend of parameter(s) Y. Subsequently, depending on the results of tests 4 and 5, normal, hypervigilant or overt alarm conditions may be generated. If sensitive tests 4 pass, normal conditions prevail; paused actions are resumed or initiated actions are canceled, silent or semi-overt alarms are turned off and there is a general "stand down". If sensitive tests 4 fail but specific tests 5 pass, then hypervigilant conditions that may include paused or initiated actions and silent or semi-overt alarms are in effect. If both sensitive tests 4 and specific tests 5 fail, overt alarm conditions and stoppage of actions remain enforced. The embodiment previously described comprises three preparedness conditions: normal, hypervigilant and overt alarm. The invention contemplates more than three levels of preparedness such as, for example, a plurality of gradations of hypervigilant conditions, interposed between normal and overt alarm conditions.

Figure 2:
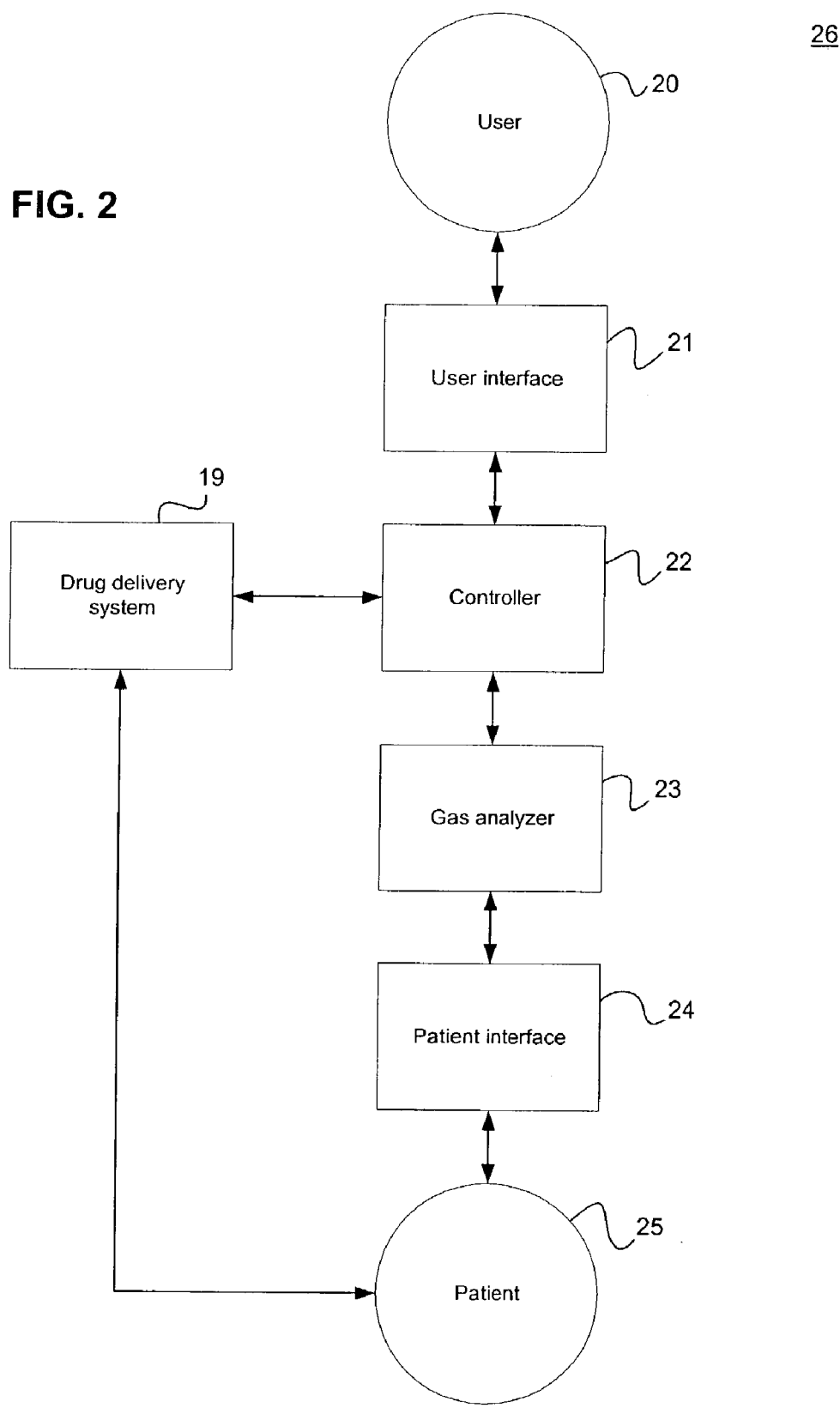
FIG. 2 illustrates a block diagram depicting one embodiment of a gas analyzer integrated with a drug delivery system in accordance with the present invention.

FIG. 2 illustrates one embodiment of an integrated gas analysis and drug delivery system 26 comprising user interface 21, controller 22, gas analyzer 23, patient interface 24, and drug delivery system 19. Drug delivery system 19 comprises delivering one or a plurality of drugs by one or a plurality of drug delivery devices, such as, for example, pumps. User 20 operates integrated gas analysis and drug delivery system 26 in order to monitor gas exchange occurring in patient 25. In a further embodiment of the present invention, integrated gas analysis and drug delivery system 26 provides an early response that deactivates all or part of drug delivery system 19 when hypoventilation is detected. Examples of drug delivery system 19, user interface 21, patient interface 24, and controller 22, which may be used with the present invention, are disclosed in U.S. patent application Ser. No. 09/324,759, filed Jun. 3, 1999 which is herein incorporated by reference in its entirety.

The present invention further comprises a plurality of means for monitoring and/or maintaining sufficient gas exchange, including, but not limited to, systems for use with intubated patients, full mask monitoring systems, systems introducing oxygen orally and/or nasally, and systems that selectively monitor a preferred airway path of patient 25.

User 20 may be an anesthesiologist, a certified registered nurse anesthetist (CRNA) or, in the case of a sedation and analgesia system, a trained non-anesthetist practitioner. One embodiment of the present invention comprises use of integrated gas analysis and drug delivery system 26 to deliver anesthesia, monitored anesthesia care, sedation, and/or analgesia with an associated pause in delivery of selected drugs that have a potential to cause respiratory depression upon detection of hypoventilation. However, other means of monitoring respiration are contemplated for use with the present invention for the detection of hypoventilation. Examples of such means are monitors of airway pressure, sound, temperature, humidity, intermittent water condensation on a polished end of an optical fiber leading to changes in refraction, chest movement, spirometry and transthoracic impedance plethysmography, among others. Monitoring respiration via airway pressure has advantages in decreasing response time of the system over some embodiments employing capnometers because of the relative time delay associated with the transport delay in sidestream capnometers. Further, it is contemplated that trained individuals may use the system and method of the present invention in a plurality of procedures, such as, for example, cardiac catheterization, colonoscopy and endoscopy where the benefits of reliable and early detection of hypoventilation are desirable. User 20 interacts with gas analysis and drug delivery system 26 via user interface 21. User interface 21 comprises data displayed in the form of "real-time" graphical data, numeric data, and/or a printed hard copy relating to ventilation. An example of such a user interface is disclosed in U.S. patent application Ser. No. 10/285,689 filed Nov. 1, 2002, and incorporated herein by reference in its entirety.

Controller 22 may be a CPU, or any other suitable data processing system. The software executed by controller 22 is coded in a language such as, for example, C or C++ under an operating system such as, for example, QNX. However other operating systems such as, for example, LINUX, VX Works, or Windows Embedded NT are consistent with the present invention. Certain embodiments operate in a real time operating system such as, for example, QNX, where programs relating to specific patient interfaces, user interfaces, capnometry, and other features of integrated gas analysis and delivery system 26 are compartmentalized into separate program modules (not shown). As will be disclosed herein, controller 22 further comprises programming related to gas analysis, activation and deactivation of all or part of drug delivery system 19, and oxygen delivery.

In one embodiment of the present invention gas analyzer 23 is a capnometer that is integrated with integrated gas analysis and drug delivery system 26. Embodiments of capnometer 23 comprise nasal carbon dioxide monitors, oral carbon dioxide monitors, sidestream aspirating capnometers, mainstream capnometers, or other suitable capnometers such as, for example, infrared, Raman scattering and mass spectrometer.

Figure 3:
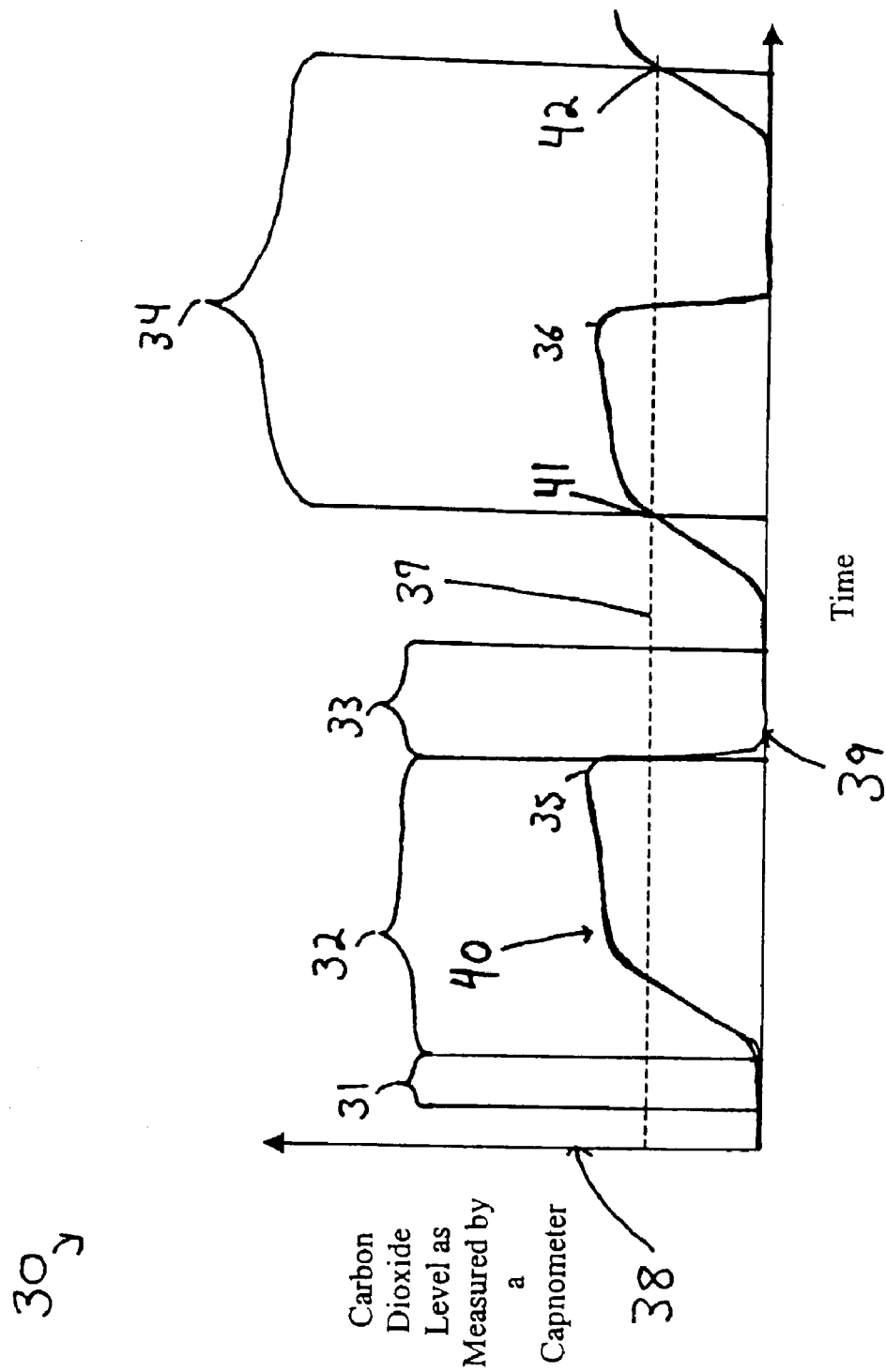
FIG. 3 illustrates one embodiment of a capnogram feature extraction algorithm in accordance with the present invention.

FIG. 3 illustrates one embodiment of a capnogram feature extraction algorithm 30 in accordance with the present invention comprising carbon dioxide level measured by a capnometer on y-axis 38, time on x-axis 39, carbon dioxide waveform (capnogram) 40, and carbon dioxide threshold 37, where capnogram feature extraction algorithm 30 is used to determine respiratory rate. An exhalation component of capnogram 40 comprises three phases: phase I 31, phase II 32 and phase III 33. The peak $CO_2$ values in phase III are end-tidal $CO_2$ concentrations 35 and 36 that are generally interpreted as representative of $P_aCO_2$.

In one embodiment of the present invention, carbon dioxide threshold 37 is established, where respiratory cycle time 34 is measured from point 41 where exhaled $CO_2$ first crosses carbon dioxide threshold 37 on an upstroke, to point 42 where exhaled $CO_2$ again crosses carbon dioxide threshold 37 on an upstroke. Other $CO_2$ thresholds (not shown) may also be used with the present invention for other functions, for example, to set low and high alarm limits for $P_{et}CO_2$. The present invention further comprises respiratory cycle time 34 calculated from a time interval between peak $CO_2$ value 35 in phase III of one breath and peak $CO_2$ value 36 in a following breath, a first inhalation until a second inhalation, a time interval between similar distinctive and unique landmarks in consecutive capnograms or by any other suitable means of calculating a respiratory cycle time. If a patient does not exhale a sufficient amount of carbon dioxide in a predetermined period of time, capnometer 23 may signal controller 22 of the possibility of hypoventilation. In one embodiment of the present invention, capnogram feature extraction algorithm 30 is used in cooperation with a method for detecting hypoventilation and apnea monitoring 50 (FIGS. 5, 5B, 5C, 5D), as will be illustrated herein, while diminishing the incidence of annoying false positive and/or potentially life-threatening false negative alarms.

Figure 4:
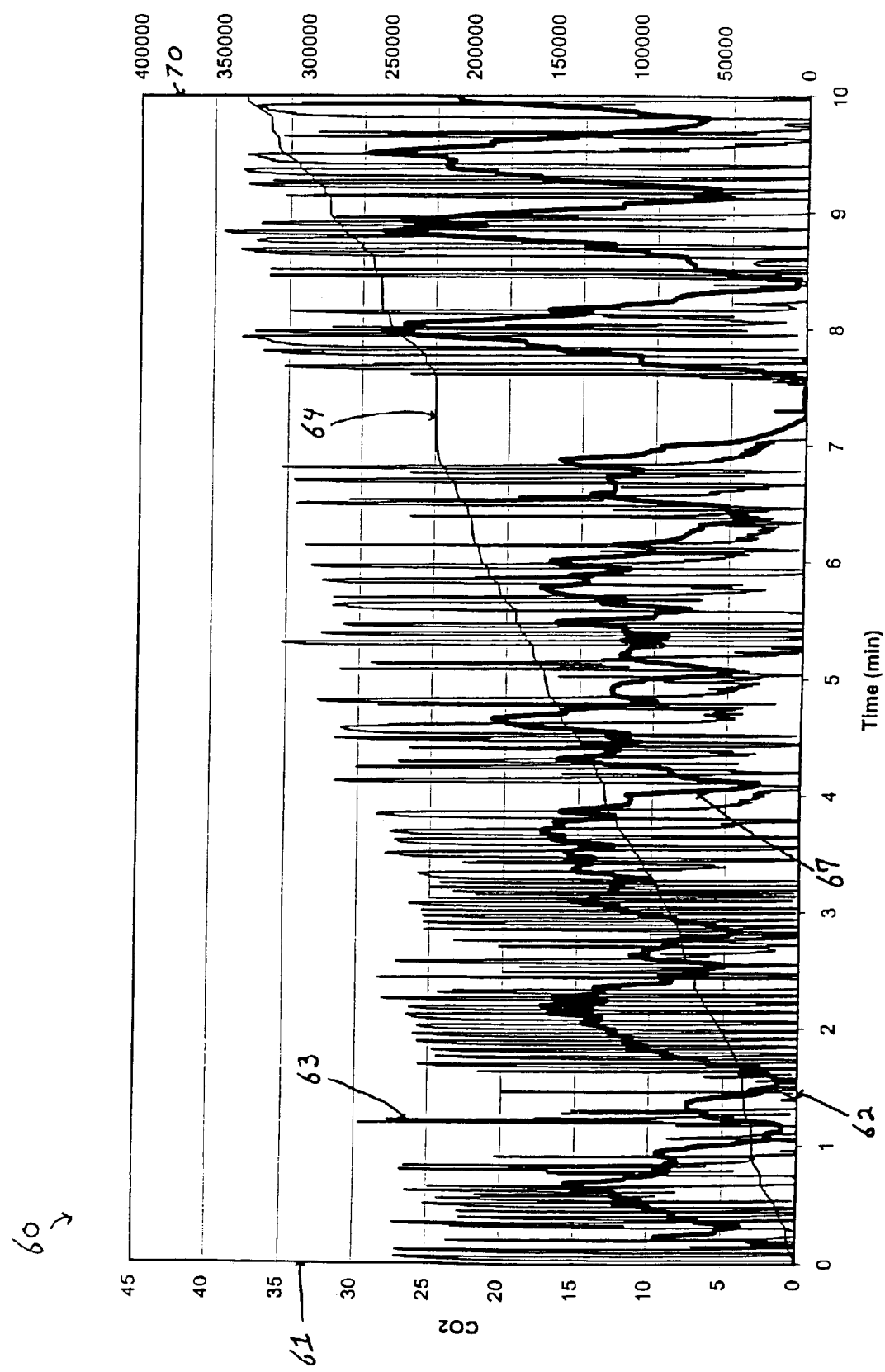
FIG. 4 illustrates one embodiment of a method of gas analysis, display and interpretation in accordance with the present invention.

FIG. 4 illustrates one embodiment of displaying and analyzing capnogram 60 in accordance with the present invention comprising partial pressure of $CO_2$ ($pCO_2$) in mm Hg on left y-axis 61, time in minutes on x-axis 62, waveform 67 of $pCO_2$ averaged over a moving time window of the most recent, for example, 12 seconds, waveform 63 of instantaneous $pCO_2$, waveform 64 representing a cumulative sum of $pCO_2$ starting at time t=0 minutes, and cumulative $pCO_2$ in units of mm Hg on right y-axis 70. Respiratory waveform 63 illustrates a plurality of respiratory cycles 34 measured in terms of partial pressure of $CO_2$ in mm Hg. However measuring carbon dioxide concentration as a fraction of overall gas concentration such as, for example, volume/volume, weight/weight, weight/volume, volume/weight, or by other suitable means, is consistent with the present invention. Averaged $pCO_2$ waveform 67 comprises, in the illustrated example, an average of $pCO_2$ over the previous or most recent 12 seconds. However averaging time periods other than 12 s, such as, for example, 20, 30 and 40 seconds, are consistent with the present invention. Cumulative $pCO_2$ waveform 64, measured relative to cumulative $pCO_2$ right y-axis 70, comprises a sum of all sampled $pCO_2$ values over the course of an entire procedure or over a specific time period. The present invention further comprises an addition of a plurality of averaged waveforms relating to method 100 (FIG. 6), numeric data, or other suitable means of illustrating data.

Figure 5A:
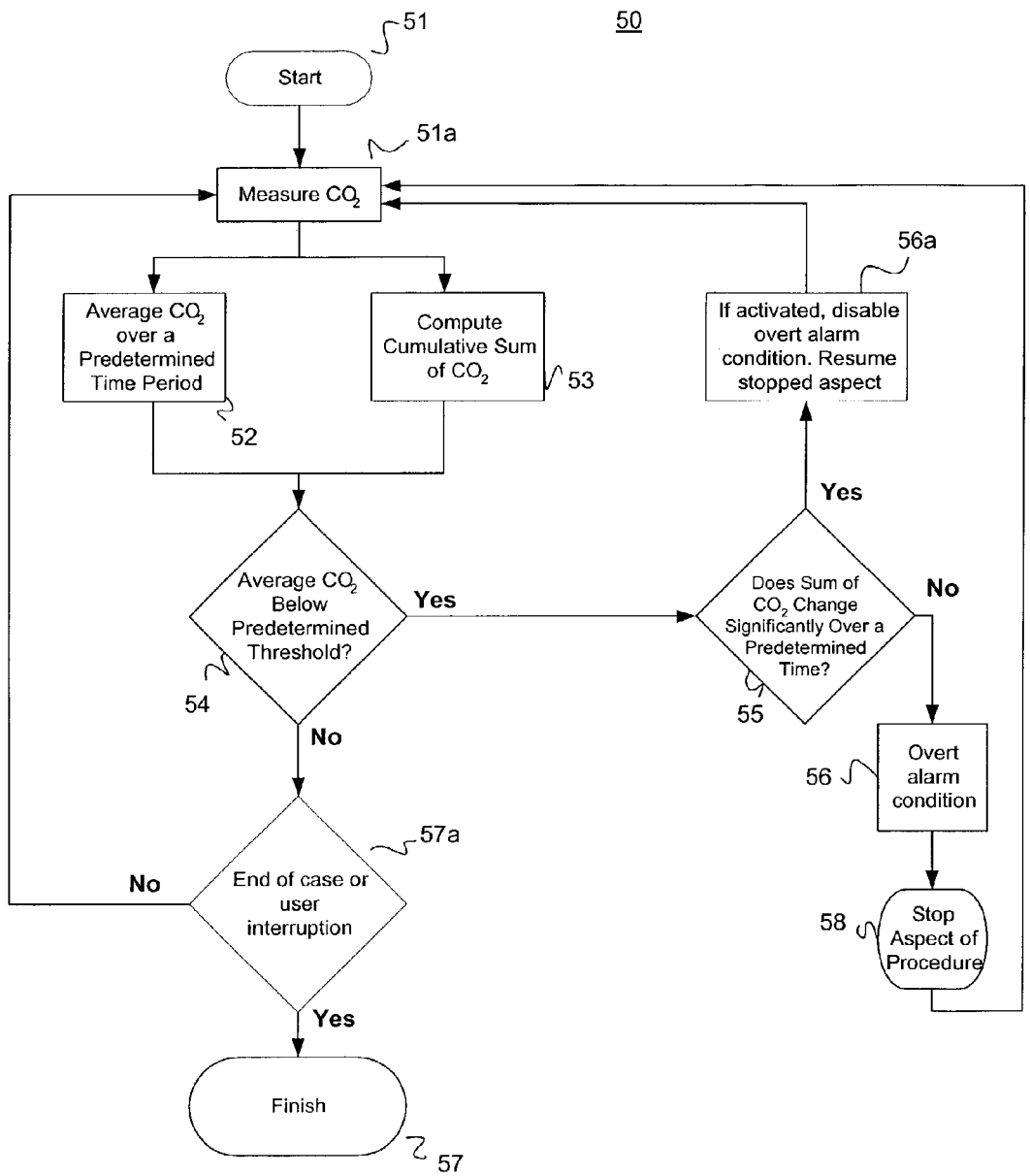
FIG. 5a illustrates a flow chart depicting one embodiment of a method of generating hypervigilant conditions, alarm conditions and predetermined responses based on gas analysis in accordance with the present invention.
Figure 5B:
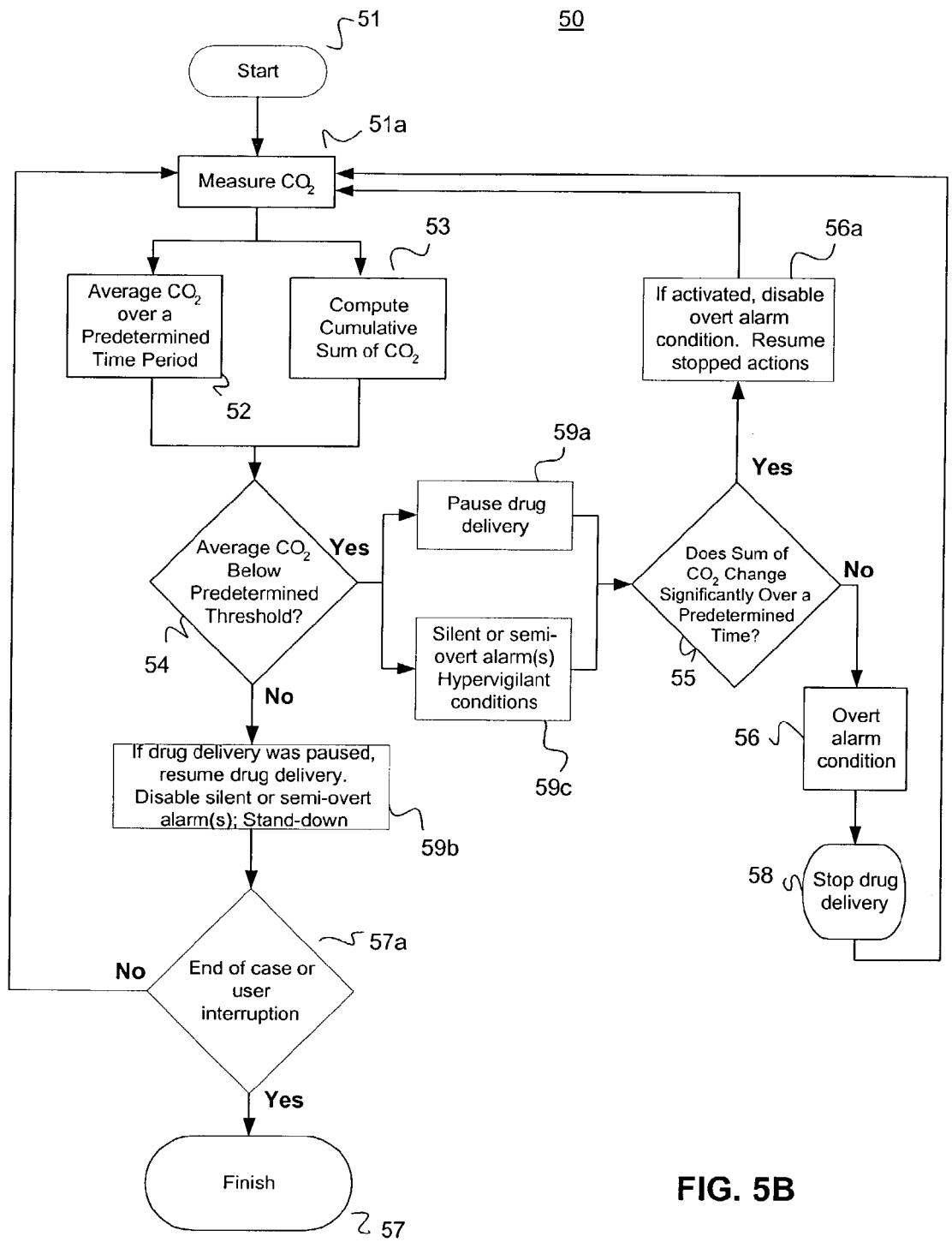
FIG. 5b illustrates a flow chart depicting an alternative embodiment of a method of generating hypervigilant conditions, alarm conditions and predetermined responses, including a drug pause, based on gas analysis in accordance with the present invention.

FIG. 5A illustrates one embodiment of a method 50 for providing hypoventilation detection and apnea monitoring comprising the steps of: start 51 of the procedure, averaging 52 of partial pressure of carbon dioxide over a predetermined period of time to obtain average $pCO_2$ plot 67 and computing 53 a cumulative sum of $pCO_2$ that is used for plot 64. Method 50 further comprises a standing query 54 whether average $pCO_2$ 67 is below a predetermined threshold, which may stand through to the finish 57 of a procedure. A "yes" answer to query 54 prompts an assessment 55 whether, from a time of that "yes" response to query 54 forward, a cumulative sum of $pCO_2$ changes significantly over a predetermined period of time, representing for example, two good breaths with full exhalations in 20 seconds. In one embodiment of the present invention, after a "yes" to query 54, a step of a procedure for which method 50 is provided may be automatically paused while query 55 is issued. For instance, as FIGS. 5B and 5D show, an administration of one or more drugs that have the potential to cause hypoventilation may be paused ("drug pause") while query 55 proceeds. A "no" answer to query 55 prompts overt alarm condition 56, which may lead to halting 58 of an aspect of a procedure, such as, for example, stopping one or more drugs. Following steps 56 and 58, method 50 loops back to step 51 a of measuring $pCO_2$ and executes once more query 54 to determine if average $pCO_2$ is below a predetermined threshold.

A "yes" answer to query 55 results in step 56a (FIGS. 5A, 5B, 5C, 5D) that removes overt alarm condition 56 and interruption 58 of an aspect of a procedure; method 50 loops back to measurement of $CO_2$ 51a and remains in a hyper-vigilant mode with drug pause and/or silent or semi-overt alarms remaining in effect as long as query 54 indicates that a sensitive test for hypoventilation is positive. For example, in one embodiment of method 50, if a predetermined threshold for average $pCO_2$ requires an average $pCO_2$ of 1 mm Hg over a ten second period, and a patient does not meet this threshold, drug delivery may be paused momentarily without an alarm necessarily sounding, thus acting as a silent response to a developing condition that could be harmful to the patient. A cumulative sum of $pCO_2$ may then be required to add to a sum total of, for example, 4,000 mm Hg (equivalent to two good breaths with full expirations) over, for example, a twenty second period at a given sampling rate, such as, for example, 50 Hz, in order to obviate an overt alarm and/or an interruption of drug delivery. It is to be noted that the actual value of a threshold for predetermined change in cumulative $pCO_2$ over a given time period is dependent on the sampling frequency of $CO_2$ measurement. Other suitable average and cumulative $pCO_2$ thresholds are consistent with the present invention, especially at different sampling frequencies of $CO_2$ measurement.

If part or all of drug delivery system 19 has been paused due to a "yes" answer to query 54, a subsequent "no" answer to query 54 causes part or all of drug delivery system 19 to resume suspended operations (FIGS. 5B, 5D); silent or semi-overt alarms are also cancelled (FIGS. 5A, 5B, 5C, 5D). Method 50 subsequently executes query 57a to verify if controller 22 or user 20 has requested an end of case or interruption. If an answer to query 57a is "no", method 50 loops back to measurement of $CO_2$ 51a. If an answer to query 57a is "yes", method 50 transitions to finishing step 57 which comprises deactivation of integrated gas analysis and drug delivery system 26.

Averaging of $pCO_2$ 52 comprises measuring the $pCO_2$ associated with patient 25 via patient interface 24. Data relating to $pCO_2$ levels associated with patient 25 is then transmitted to controller 22, where controller 22 is programmed to calculate average levels of $pCO_2$, for a predetermined time period. For example, controller 22 may be programmed to calculate an average $pCO_2$ level over a previous or most recent twelve-second period or moving time window. Averaging data over a moving time window of predetermined duration diminishes the effects of artifacts (spurious or invalid data) and presents user 20 and controller 22 with a more accurate reflection of an actual ventilatory status of patient 25 over the moving time window. The moving time window for averaging $pCO_2$ may be any length of time suitable to ensure patient safety, exhibiting a compromise between artifact filtering (generally improved by longer time windows) and response time (generally improved by shorter time windows). Weighted averages are also possible, where weights are used to emphasize or reduce an effect of $pCO_2$ values from a selected portion of a moving time window. For example, to emphasize $pCO_2$ values for the most recent 2 seconds within a 12 s moving average, all $pCO_2$ values from the most recent 2 seconds may be multiplied by a weight n, where n is greater than 1, before being included in the averaging process. An amount by which a weight n is greater than 1 will determine how much emphasis is provided to a desired time segment within a moving time window. A weighted time segment could be at any desired point in a moving time window. A time segment of the most recent 2 seconds was only used by way of an example and should not be considered limiting.

Step 53 comprises computing a cumulative sum of $pCO_2$, that is, adding a sum of all sampled $pCO_2$ values throughout a procedure or during a specified time period. In one embodiment of the present invention, controller 22 may be programmed to compute and/or display average $pCO_2$ 67 and cumulative $pCO_2$ 64 simultaneously.

Query 54 comprises setting a predetermined threshold and determining whether an average $pCO_2$ measured over a predetermined time period and obtained from averaging step 52, is above or below a predetermined threshold. Levels of carbon dioxide may be measured in partial pressure, as a fraction of expired or inspired gas, or by any other suitable means. A predetermined threshold consistent with query 54 may be expressed as a partial pressure, as a fraction of expired and inspired gas, or as any other suitable benchmark. In one embodiment of the present invention, a predetermined threshold is established such that average $pCO_2$ levels below it are indicative of a potentially life threatening situation. In particular, if gas levels exhaled by patient 25 are associated with average $pCO_2$ levels below a threshold, patient 25 may be experiencing a correspondingly low amount of gas exchange, resulting in a potentially dangerous situation. By averaging data for carbon dioxide levels over a predetermined moving time window, the present invention provides an accurate indicator as to whether a patient is indeed experiencing a low level of gas exchange when average $pCO_2$ drops below a predetermined threshold.

Figure 5C:
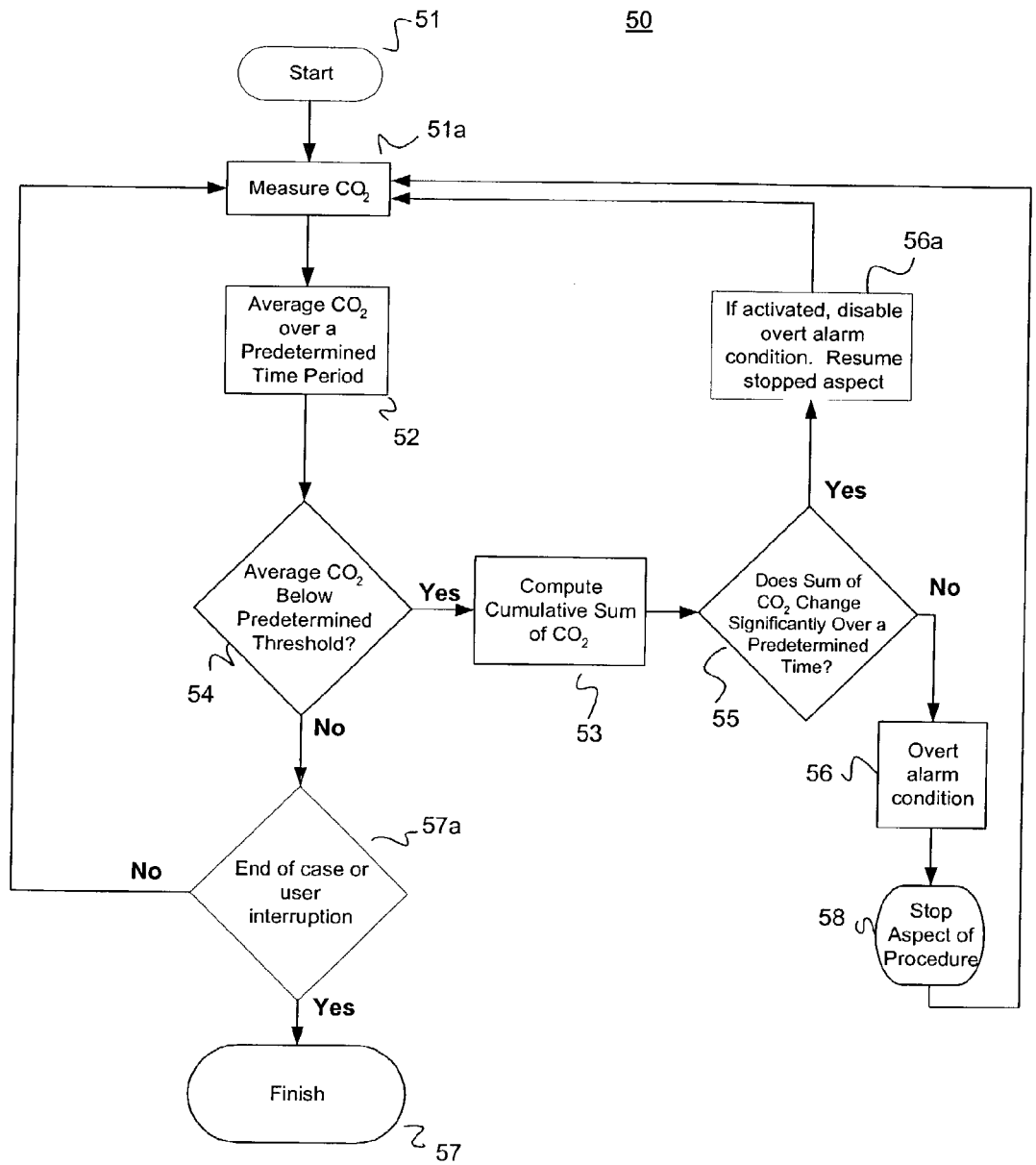
FIG. 5c illustrates a flow chart depicting an alternative embodiment of a method of generating hypervigilant conditions, alarm conditions and predetermined responses based on gas analysis in accordance with the present invention.
Figure 5D:
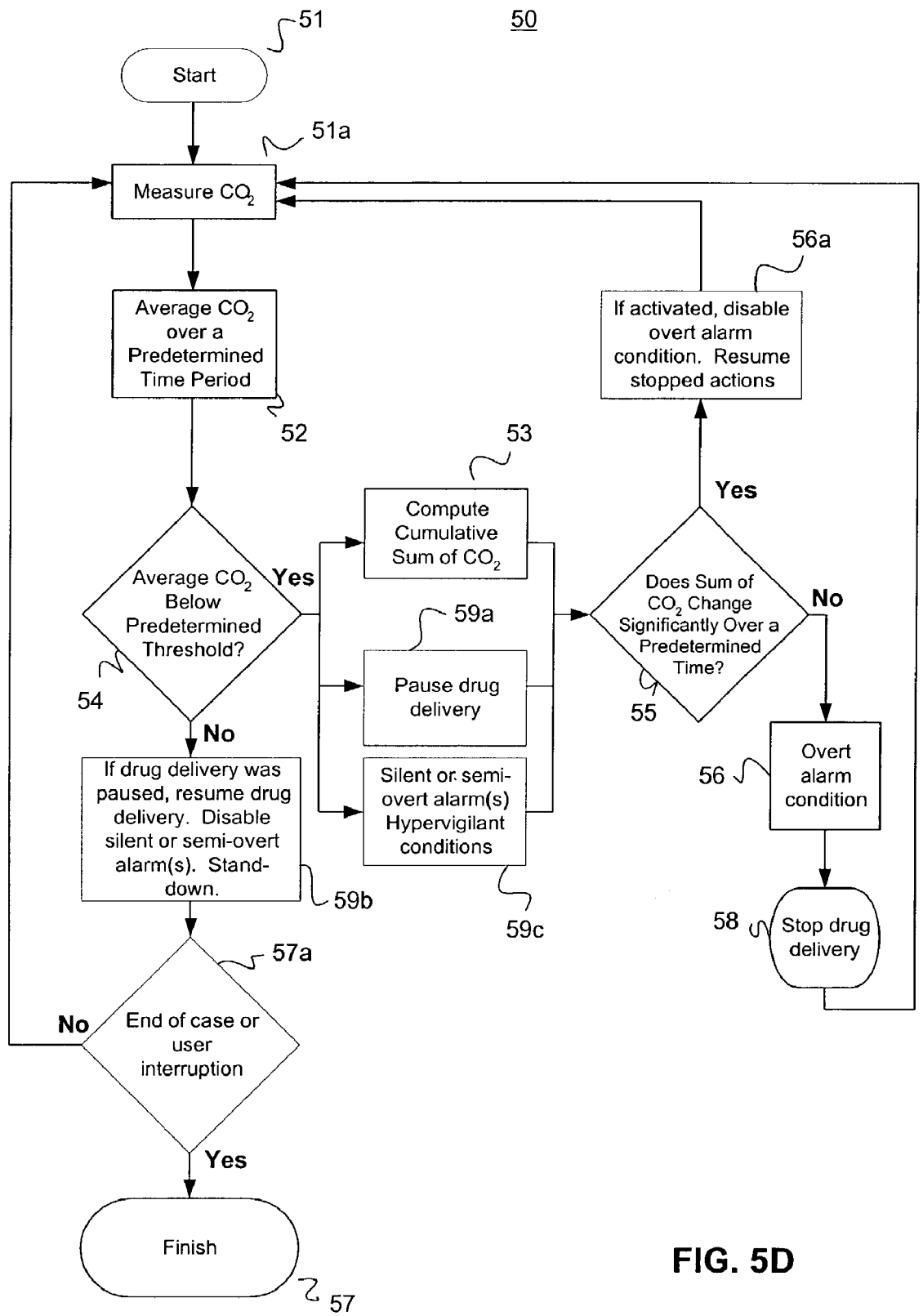
FIG. 5d illustrates a flow chart depicting an alternative embodiment of a method of generating hypervigilant conditions, alarm conditions and predetermined responses, including a drug pause, based on gas analysis in accordance with the present invention.

If an answer to query 54 is "no", method 50 proceeds to measurement of $CO_2$ 51a if there is no end of case or user interruption and continues to average $pCO_2$ levels and to cumulatively sum $pCO_2$ (FIGS. 5A, 5C). If the answer is "yes" to query 54, integrated gas analysis and drug delivery system 26 executes query 55 to determine if a cumulative sum of carbon dioxide, starting at a time when execution of step 55 is begun, changes significantly over a predetermined time (FIG. 5A). Query 55 comprises controller 22 computing a change in a cumulative sum of carbon dioxide according to step 53 for a period of time after an average $pCO_2$ falls below a predetermined threshold. In effect, query 55 functions to look ahead, prospectively anticipating future events, whereas query 54 looks back to determine retrospectively whether a past average $pCO_2$ is above or below a predetermined threshold. Unlike an average $pCO_2$ value, a change in a cumulative sum starting at a time of failure of a sensitive test is not weighted down by past history of the $pCO_2$ level, thus jettisoning past history of $pCO_2$ to provide faster response while still remaining fairly immune to artifacts. In one embodiment of the present invention, following a drop in average $pCO_2$ below a threshold, integrated gas analysis and drug delivery system 26 looks to the overall change in a cumulative sum of $pCO_2$ for a period of time to determine whether the change in the cumulative sum of $pCO_2$ rises enough to indicate that sufficient gas exchange is occurring. Like a predetermined threshold, an amount of increase in a cumulative sum of $pCO_2$ needed to indicate sufficient gas exchange, and a time period over which an increase in cumulative $PCO_2$ is anticipated, may be established by user 20, by programming associated with controller 22, or by other suitable means of establishing the aforementioned parameters.

Further embodiments of the present invention comprise calculating a cumulative sum of $pCO_2$ only after query 54 has been answered "yes", and discontinuing calculation of the cumulative sum of $pCO_2$ when a "no" response is given to query 54 as illustrated in FIGS. 5C and 5D.

If there is a significant increase in cumulative $pCO_2$ after dropping below a predetermined threshold for $pCO_2$ average, method 50 will proceed through a hypervigilant path which incorporates step 51a of measuring $CO_2$ and query 54 as to whether an average $pCO_2$ is below a threshold. If an answer to query 54 is "no", method 50 proceeds through a normal and uneventful path. If there is no significant increase in a cumulative sum of $pCO_2$ during a predetermined time period, query 55 will transition to alarm condition 56. Query 54 and query 55 provide integrated gas analysis and drug delivery system 26 with a dual means of detecting inadequate gas exchange. The prospective nature of one detection means (such as, for example, cumulative sum) complements the retrospective nature of another detection means (such as, for example, time averaging). Similarly, the sensitivity of test 54 complements the specificity of test 55. The present invention diminishes the incidence of false positive and false negative alarms by providing a rigorous querying process. A significant increase of a cumulative sum of $pCO_2$ required to obviate alarm condition 56 may be a required percentage increase from a point in time when query 55 begins, a specific numerical increase from a point in time when query 55 begins, or any other suitable means of indicating a patient is experiencing sufficient alveolar gas exchange.

In one embodiment of the present invention, alarm condition 56 comprises an alarm signaling user 20 and a response of deactivating drug delivery system 19 (FIGS. 5B, 5D). It should be noted that drug delivery system 19 will already be paused when query 55 is executed as a result of a "no" answer to query 54 (FIGS. 5B and 5D). Deactivation of drug delivery system 19, as a result of alarm condition 56, is an extension of a "drug pause" in drug delivery system 19. Signaling user 20 comprises audio alarms, visual alarms, or other suitable signaling means. Deactivation of drug delivery system 19 includes, but is not limited to, partial or total deactivation of intravenous drug delivery, partial or total deactivation of systemic drug delivery, and/or partial or total deactivation of inhalation drug delivery. Halting drug delivery may alleviate complete or partial airway obstruction due to overmedication. Following partial or total deactivation of drug delivery system 19, integrated gas analysis and drug delivery system 26 will, in one embodiment of the present invention, loop back to $CO_2$ measurement 51a and continue on to query 54. If the answer to query 54 is still "yes", query 55 is executed. Then, following a "yes" response to query 55, integrated gas analysis and drug delivery system 26 will move out of alarm condition 56 and re-activate an aspect of a procedure that was halted. A further embodiment of the present invention comprises deactivating integrated gas analysis and drug delivery system 26 in the event of alarm condition 56. Further embodiments of the present invention comprise gas analysis and drug delivery system 26 moving out of alarm condition 56 when average $pCO_2$ levels over a predetermined time period exceed a predetermined threshold, when a cumulative sum of $pCO_2$ increases at a predetermined rate, or beyond a predetermined percentage threshold over a given time period, and/or when combinations of average $pCO_2$ and cumulative sum of $pCO_2$ reach predetermined levels. Alarms may alert user 20 to a potential negative patient episode in a variety of means such as, for example, by way of the user interface disclosed in U.S. patent application Ser. No. 10/285,689.

Method 50 for providing hypoventilation detection and apnea monitoring reduces the incidence of false positive alarms by evaluating average $pCO_2$ data in the context of cumulative $pCO_2$ data. A drop in expired $pCO_2$ related to patient phonation may be sufficient to set off alarms in existing capnometry systems. The present invention averages data over a time period to obviate false positive alarms due to artifact or data unrelated to patient ventilation. The present invention further provides a user with a dependable gas analysis and apnea monitoring system by relating averaged $pCO_2$ to cumulative sum of $pCO_2$. By considering a cumulative sum of $pCO_2$, the present invention diminishes the incidence of false positive alarms occurring in existing systems where exhalations do not exceed a predetermined threshold, yet are sufficient for adequate gas exchange.

Figure 6:
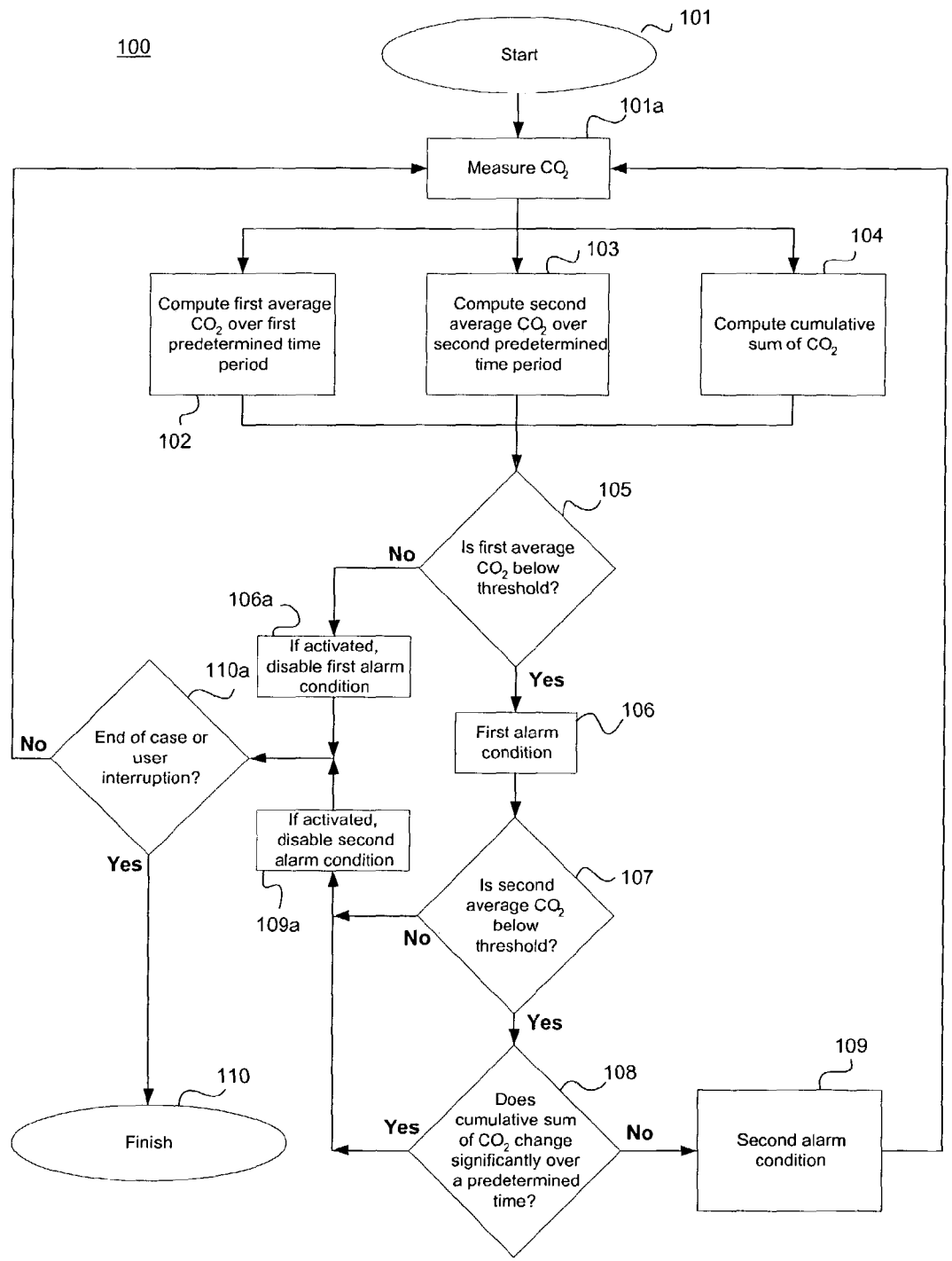
FIG. 6 illustrates a flow chart depicting an alternate embodiment of a method of generating hypervigilant conditions, alarm conditions and predetermined responses based on gas analysis, including averaging over multiple predetermined time periods, in accordance with the present invention.

FIG. 6 illustrates one alternative embodiment of a method 100 for providing hypoventilation detection and apnea monitoring comprising the steps of: start 101, $CO_2$ measurement step 101a, computing step 102 for determining a first average of $pCO_2$ over a first predetermined period of time, computing step 103 for determining a second average of $PCO_2$ over a second predetermined period of time, step 104 for computing a cumulative sum of $pCO_2$, step 105 for querying whether a first $pCO_2$ average is below a predetermined threshold, where a "no" answer prompts step 110a of checking for an end of case or interruption, and where a "yes" answer to query 105 prompts the first alarm condition in step 106, step 107 for querying whether a second average of $pCO_2$ is below a predetermined threshold, where a "no" answer prompts step 110a, and a "yes" answer prompts step 108 for querying if a cumulative sum of $pCO_2$ then changes significantly over a predetermined period of time, where a "yes" answer to query 108 prompts step 110a and a "no" answer prompts second alarm condition 109. In one embodiment of the present invention, second alarm condition 109 returns to $CO_2$ measurement step 101a. Finish 110 comprises deactivation of integrated gas analysis and drug delivery system 26 by user 20 or by controller 22, deactivation during second alarm condition 109, or deactivation at any desirable point of method 100. A "no" response to query 110a indicates that there is no request for program interruption and method 50 loops back to $CO_2$ measurement 101a. From step 101a, method 100 may perform any or all of steps 102, 103 and/or 104.

Step 102 comprises establishing a predetermined period of time such as, for example, twelve seconds, for which an average $pCO_2$ is calculated. Step 102 comprises any suitable predetermined period of time for averaging $pCO_2$.

Step 103 comprises establishing a predetermined period of time such as, for example, forty seconds, for which an average $pCO_2$ is calculated. In one embodiment of the present invention, a predetermined time period of step 103 is longer than a predetermined time period established for step 102.

Step 104 comprises computing a cumulative sum of $pCO_2$ throughout a procedure or during a given time period. In one embodiment of the present invention, controller 22 may be programmed to calculate and/or display a first average of step 102, a second average of step 103, and a cumulative sum of $pCO_2$ of step 104 simultaneously.

Query 105 comprises establishing an average $pCO_2$ threshold, where a measured average $pCO_2$ below the established threshold indicates potentially insufficient alveolar gas exchange. An established threshold may be any level indicative of a critical average $CO_2$ benchmark, and may be established as a partial pressure, a fraction of expired and inspired gas, or as any other suitable unit of measurement. If a response to query 105 is "no", method 100 transitions to step 110a. If the response to query 105 is "yes", integrated gas analysis and drug delivery system 26 moves to first alarm condition 106. One embodiment of the present invention comprises calculating and/or displaying averages and/or sums relating to steps 102, 103, and/or 104 throughout the duration of method 100.

In one embodiment of the present invention, first alarm condition 106, herein referred to as step 106, comprises deactivating part or all of drug delivery 19, an increased monitoring frequency of patient parameters with optionally tighter alarm bounds, and alerting user 20 of an alarm condition. In one embodiment of the present invention, step 106 comprises deactivating part or all of drug delivery 19, but user 20 is not informed of a transition to first alarm condition 106, minimizing user distraction.

The present invention comprises utilizing a first average (step 102) measured over a relatively short predetermined time period such as, for example, twelve seconds, where a drop in average $pCO_2$ will be detected quickly. As a predetermined time period for averaging $pCO_2$ becomes shorter, the likelihood of a false positive alarm becomes higher due to an increase in sensitivity to artifact or spurious data. In one embodiment of the present invention, method 100 comprises exploiting the benefits of highly sensitive measurement, such as, for example, a diminished incidence of false negative alarms, in conjunction with an increased specificity gained by using longer time averages (step 103) of $pCO_2$. To this effect, first alarm condition 106 is triggered upon first average $pCO_2$ (step 102) dropping below a predetermined threshold. First alarm condition step 106, in one embodiment of the present invention, deactivates part or all of drug delivery 19 but does not inform user 20 that method 100 has entered first alarm condition 106. In doing so, delivery of drugs that may have adverse effects on ventilation is discontinued without initiating an overt visual or audio alarm. A pause of part or all of drug delivery system 19 may be a response to a false positive alarm, resulting from a high sensitivity of a first average $pCO_2$ (step 102). Method 100 may reactivate part or all of drug delivery system 19 and deactivate first alarm condition 106 if it was previously enabled, upon receipt of a "no" response to query 105. Pausing of part or all of drug delivery system 19 as a response to a false positive alarm for a brief interval while awaiting further diagnostic information to more fully define ventilatory status has no harmful effect, yet provides greater patient safety due to an "early response" intervention in the form of a drug pause in the event that a first alarm condition develops into a bona-fide emergency. This is especially so with drugs whose effects are not immediately discontinued as soon as drug administration is turned off and benefits accrue from early intervention so that a patient can thus recover earlier from a hypoventilation or apneic episode, possibly without a user even being aware of an early intervention. To minimize the risk of silent or semi-overt interventions being masked by methods 100 or 50, these interventions may be logged by integrated gas analysis and drug delivery system 26 and may be available for review and quality assurance purposes. Method 100 continues to query more specific averages (query 107), as opposed to more sensitive averages, in determining whether a potentially life-threatening situation truly exists. If, for example, query 105 detects sufficient gas exchange upon a first average (step 102) exceeding a predetermined threshold, part or all of drug delivery system 19 may be reactivated with no negative patient effect caused by a partial or total pause in drug administration. A further embodiment of the present invention comprises second alarm condition 109 returning to query 108, where if the answer is "yes", step 106a of deactivating the second alarm condition is executed.

Query 107 comprises setting a predetermined threshold and determining whether a second average of $pCO_2$ (step 103), measured over a predetermined time period, is above or below a predetermined threshold. Levels of carbon dioxide may be measured in partial pressure, as a fraction of expired or inspired gas, or by any other suitable means. A predetermined threshold may be established as a partial pressure, as a fraction of expired or inspired gas, or as any other suitable benchmark. In one embodiment of the present invention, a predetermined threshold is established at a level such that average $pCO_2$ values below the threshold are indicative of a potentially life threatening situation. In one embodiment of the present invention, a predetermined time period of a second average (step 103) is longer than a predetermined time period of a first average (step 102) in order to provide increased specificity. By providing a relatively long predetermined time period for a second average (step 103), method 100 diminishes the incidence of false positive alarms due to data artifact.

If the answer to query 107 is "no", integrated gas analysis and drug delivery system 26 remains in first alarm condition 106. If the answer to query 107 is "yes", integrated gas analysis and drug delivery system 26 executes query 108 to determine if a cumulative sum of $pCO_2$ changes significantly over a predetermined time. Query 108 comprises controller 22 evaluating data computed in step 104 for a period of time after first or second average $pCO_2$ falls below a predetermined threshold. In effect, query 108 functions to look ahead, anticipating future events, whereas query 107 looks back to determine whether a second average (step 103) of $pCO_2$ is above or below a predetermined threshold. In one embodiment of the present invention, following a drop in a second average (step 103) of $pCO_2$ below a threshold, integrated gas analysis and drug delivery system 26 looks to a cumulative sum of $pCO_2$ for a period of time to ascertain whether the cumulative sum rises enough to indicate sufficient gas exchange. As with a predetermined threshold, an amount of increase in a cumulative sum of $pCO_2$ needed to indicate sufficient gas exchange, and a time period over which the increase is anticipated, may be established by user 20, by programming associated with controller 22, or by other suitable means of establishing the aforementioned parameters.

A further embodiment of the present invention comprises calculating a cumulative sum of $pCO_2$ only after query 107 has been answered "yes", and discontinuing calculation of a cumulative sum of $pCO_2$ when a "no" response is given to query 107. This further embodiment would move the cumulative summing step 104 such that it is located between queries 107 and 108.

If there is a significant increase of cumulative $pCO_2$ after dropping below a predetermined threshold associated with query 107, method 100 loops back to $CO_2$ measurement step 101a. If there is not a significant increase in a cumulative sum of $pCO_2$ during a predetermined time period, query 108 responds with second alarm condition 109. Query 105, query 107, and query 108 provide integrated gas analysis and drug delivery system 26 with redundant means of detecting inadequate gas exchange while diminishing the incidence of annoying false positive and potentially life-threatening false negative alarms. The present invention diminishes the incidence of false positive and false negative alarms by providing a rigorous querying process. A significant increase of a cumulative sum of $pCO_2$ required to obviate second alarm condition 109 may be a required percentage increase from a point in time when query 108 begins, a specific numerical increase from a point in time when query 108 begins, or any other suitable means of assuring a patient is experiencing sufficient gas exchange. Query 107 and query 108 provide the present invention with increased specificity in determining whether patient 25 is experiencing a truly life-threatening episode. Pausing of part or all of drug delivery system 19, associated with first alarm condition 106, places patient 25 into a safe state while query 107 and 108 determine true ventilatory status. By placing patient 25 into a drug deactivated or paused safe state, integrated gas analysis and drug delivery system 26 combines the benefits of high-sensitivity and high-specificity in determining the true seriousness of an alarm condition, while diminishing a probability of overdose and/or apnea due to over-medication and minimizing disruptions.

In one embodiment of the present invention, second alarm condition 109 comprises signaling user 20 and deactivating all or part of drug delivery system 19. Signaling user 20 comprises overt audio alarms, visual alarms, or other suitable signaling means. Deactivation of part or all of drug delivery system 19 includes, but is not limited to, deactivation of intravenous drug delivery, deactivation of systemic drug delivery, and/or deactivation of inhalation drug delivery. Halting delivery of drugs that may cause hypoventilation may alleviate complete or partial airway obstruction caused by over-medication. Following deactivation of part or all of drug delivery system 19 in step 109, integrated gas analysis and drug delivery system 26 will, in one embodiment of the present invention, continue to $CO_2$ measurement 101a. In one embodiment of the present invention, following a "yes" response to query 108, integrated gas analysis and drug delivery system 26 will, in step 109a, disable second alarm condition 109. A further embodiment of the present invention comprises deactivating integrated gas analysis and drug delivery system 26 in the event of second alarm condition 109. Further embodiments of the present invention comprise integrated gas analysis and drug delivery system 26 moving out of alarm condition 109 when a first average of $pCO_2$ over a predetermined time period (step 102) exceeds a predetermined threshold, when a cumulative sum of $pCO_2$ increases at a predetermined rate or beyond a predetermined percentage threshold, or when a combination of average $pCO_2$ and cumulative sum of $pCO_2$ reaches a predetermined level.

Method 100 provides increased specificity, increased sensitivity, and early deactivation of part or all of drug delivery system 19 in the event of a potentially dangerous patient episode, while diminishing the probability of false negative and false positive alarms. Method 100 further comprises integrating gas analyzer 23 with drug delivery system 19, where resulting integrated gas analysis and drug delivery system 26 may be operated by a non-anesthetist practitioner. Operability of system 26 by a non-anesthetist practitioner is facilitated by the partially-automated, safety-biased nature of ventilatory monitoring and drug delivery associated with method 100.

While exemplary embodiments of the invention have been shown and described herein, it will be obvious to those skilled in the art such embodiments are provided by way of example only. Numerous insubstantial variations, changes, and substitutions will now be apparent to those skilled in the art without departing from the scope of the invention disclosed herein by the Applicants. Accordingly, it is intended that the invention be limited only by the spirit and scope by the claims as they will be allowed.

The invention claimed is:

1. A drug delivery system for use during the performance of a medical procedure that monitors the ventilatory conditions of a patient and provides automated responses to certain of those conditions comprising:
   a respiratory gas exchange monitor including means to output monitoring data;
   a high-sensitivity alarm algorithm to process said monitoring data, wherein said high sensitivity alarm algorithm is used for detection of a potential onset of a declining ventilatory condition, as indicated by measurement of a predetermined parameter;
   a high-specificity alarm algorithm to process said monitoring data; and
   an automated device for controlling a drug delivery mechanism in response to said data processed by said high-sensitivity and high-specificity alarm algorithms, wherein said system reduces false positive and false negative alarms in a manner that is transparent to a user.

2. The system according to claim 1, wherein said high sensitivity alarm algorithm utilizes a moving average of said monitoring data.

3. The system according to claim 1, wherein said high specificity alarm algorithm utilizes a cumulative sum of said monitoring data.

4. The system according to claim 1, wherein said detection is used to activate a silent alarm and a hypervigilant state.

5. The system according to claim 1, wherein said detection is used to activate at least one of a semi-overt alarm and a silent alarm.

6. The system according to claim 1, wherein said detection is used to initiate an action.

7. The system according to claim 6, wherein said action may be passive intervention.

8. The system according to claim 7, wherein a discontinuation of said highly sensitive alarm activates a cessation of said passive action and a stand down from said hypervigilant condition.

9. The system according to claim 6, wherein said action may be active intervention.

10. The system according to claim 9, wherein a discontinuation of said highly sensitive alarm causes activates a cessation of said active action and a stand down from said hypervigilant condition.

11. The system according to claim 1, wherein said high specificity alarm algorithm provides a confirmation of an alarm condition resulting from said highly sensitive alarm algorithm.

12. The system according to claim 11, wherein said confirmation is used to generate an overt alarm condition.

13. The system according to claim 11, wherein said confirmation is used to conduct one of an initiation and continuation of an automated corrective action.

14. The system according to claim 1, wherein said high specificity alarm algorithm provides a contradiction, said contradiction being used to maintain said hypervigilant state so long as said alarm condition resulting from said highly sensitive alarm algorithm continues.

15. The system according to claim 1, wherein said drug delivery system is a sedation and analgesia system.

16. The system according to claim 15, wherein said respiratory gas exchange monitor measures $CO_2$ levels of said patient.

17. The system according to claim 16, wherein said drug delivery mechanism administers at least one respiratory depressant.

18. The system according to claim 17, wherein said respiratory depressant is propofol.

19. A system for safely delivering a respiratory depressant such as a sedative and/or analgesic to a patient during the performance of a medical procedure by monitoring selected medical conditions of a patient and by controlling drug delivery in response thereto, said system comprising:
   a monitor that measures selected medical parameters including means to output monitoring data regarding said medical parameters;
   a high-sensitivity alarm algorithm to process said monitoring data, wherein said high sensitivity alarm algorithm is used for-detection of a potential onset of a declining ventilatory condition, as indicated by measurement of a predetermined parameter;
   a high-specificity alarm algorithm to process said monitoring data; and
   automated means for responding to said high-sensitivity and high-specificity alarm algorithms, wherein said high sensitivity alarm algorithm is used for detection of a potential onset of an undesirable trend in said selected medical parameter and wherein said detection is used to initiate a passive intervention and wherein said system reduces false positive and false negative alarms in a manner that is transparent to a user.

20. The system according to claim 19, wherein said high sensitivity alarm algorithm utilizes a moving average of said monitoring data.

21. The system according to claim 19, wherein said high specificity alarm algorithm utilizes a cumulative sum of said monitoring data.

22. The system according to claim 19, wherein said detection is used to activate a silent alarm and a hypervigilant state.

23. The system according to claim 19, wherein said detection is used to activate at least one of a semi-overt alarm and-a silent alarm.

24. The system according to claim 19, wherein said detection is used to initiate an action.

25. The system according to claim 24, wherein said action may be passive intervention.

26. The system according to claim 25, wherein a discontinuation of said highly sensitive alarm activates a cessation of said passive action and a stand down from said hypervigilant condition.

27. The system according to claim 24, wherein said action may be active intervention.

28. The system according to claim 27, wherein a discontinuation of said highly sensitive alarm causes activates a cessation of said active action and a stand down from said hypervigilant condition.

29. The system according to claim 19, wherein said high specificity alarm algorithm provides a confirmation of an alarm condition resulting from said highly sensitive alarm algorithm.

30. The system according to claim 29, wherein said confirmation is used to generate an overt alarm condition.

31. The system according to claim 29, wherein said confirmation is used to conduct one of an initiation and continuation of an automated corrective action.

32. The system according to claim 19, wherein said high specificity alarm algorithm provides a contradiction, said contradiction being used to maintain said hypervigilant state so long as said alarm condition resulting from said highly sensitive alarm algorithm continues.

33. A drug delivery system for use during the performance of a medical procedure that monitors ventilatory conditions of a patient and provides automated responses to certain of those conditions comprising:
    means for monitoring said ventilatory conditions, wherein said monitoring means includes means to output monitoring data;
    means for processing said monitoring data using a high-sensitivity alarm algorithm, wherein said high sensitivity alarm algorithm is used for detection of a potential onset of a declining ventilatory condition, as indicated by measurement of a predetermined parameter;
    means for processing said monitoring data using a high-specificity alarm algorithm; and
    automated means for controlling a drug delivery mechanism in response to said processed data, wherein said system reduces false positive and false negative alarms in a manner that is transparent to a user.

34. The system according to claim 33, wherein said detection is used to initiate an action.

35. A method of drug delivery for use during the performance of a medical procedure that monitors ventilatory conditions of a patient and provides automated responses to certain of those conditions comprising:
    monitoring said ventilatory conditions, wherein said monitoring means includes means to output monitoring data;
    processing said monitoring data using a high-sensitivity alarm algorithm, wherein said high sensitivity alarm algorithm is used for detection of a potential onset of a declining ventilatory condition, as indicated by measurement of a predetermined parameter;
    processing said monitoring data using a high-specificity alarm algorithm; and
    controlling a drug delivery mechanism in response to said processed data, wherein said system reduces false positive and false negative alarms in a manner that is transparent to a user.

36. The method according to claim 35, wherein said detection is used to initiate an action.

37. A drug delivery system for safely delivering a respiratory depressant such as a sedative and/or analgesic to a patient during the performance of a medical procedure by monitoring the ventilatory condition of the patient and by controlling drug delivery in response thereto, said system comprising:
    a respiratory gas exchange monitor for receiving data reflecting the ventilatory condition of said patient during said surgery;
    a first alarm algorithm to process said monitoring data;
    a second alarm algorithm to continue to receive data and to further process said data in the event said first alarm algorithm indicates a suspect ventilatory condition; and
    an automated device for controlling a drug delivery mechanism to said patient in response to said data processed by said first and/or second alarm algorithms.

38. The system according to claim 37, wherein said system reduces false positive and false negative alarms in a manner that is transparent to a user.

39. The system according to claim 38, wherein said first alarm algorithm utilizes a moving average of said monitoring data.

40. The system according to claim 38, wherein said second alarm algorithm utilizes a cumulative sum of said monitoring data.

41. The system according to claim 38, wherein said first alarm algorithm is used for detection of a potential onset of a declining ventilatory condition, as indicated by measurement of a predetermined parameter.

* * * * *